US005951950A

United States Patent [19]

Fukuoka et al.

[11] Patent Number: 5,951,950

[45] Date of Patent: Sep. 14, 1999

[54] DEVICE FOR ASSAY OF LIQUID SAMPLE

[75] Inventors: Takao Fukuoka; Akio Okubo, both of Kyoto, Japan

[73] Assignee: Kyoto Daiichi Kagaku Co., Ltd., Kyoto, Japan

[21] Appl. No.: 08/895,036

[22] Filed: Jul. 16, 1997

[30] Foreign Application Priority Data

Jul. 29, 1996 [JP] Japan .................................... 8-216170

[51] Int. Cl.$^{6}$ ..................................................... G01N 33/48

[52] U.S. Cl. ............................................... 422/58; 422/100

[58] Field of Search ................................. 422/56, 58, 61, 422/102, 104, 100

[56] References Cited

U.S. PATENT DOCUMENTS 5,260,222 11/1993 Patel et al. ................................ 422/58

5,622,870 4/1997 Sizto et al. ................................ 422/58

5,728,350 3/1998 Kinoshita et al. ........................ 422/58

FOREIGN PATENT DOCUMENTS

0656420 A1 6/1995 European Pat. Off. .

WO 96/19565 6/1996 WIPO .

*Primary Examiner*—Lyle A. Alexander

*Attorney, Agent, or Firm*—Finnegan, Henderson, Farabow, Garrett & Dunner, L.L.P.

[57] ABSTRACT

A device for assay of a liquid sample. The device comprises: a support composed of an organic macromolecule, the support having a surface divided into two areas located adjacent to each other; a divider in the surface, defining the border of both areas to separate a first area from a second area; a detection layer affixed to the first area and containing a reagent; and a water-swelling layer affixed to the second area, the water-swelling layer expanding by absorbing water.

8 Claims, 2 Drawing Sheets

DEVICE FOR ASSAY OF LIQUID SAMPLE

BACKGROUND OF THE INVENTION

1. Field of the Invention

This invention relates to devices used in the assay of a liquid sample. The device of this invention is suitable for use as a clinical diagnostic device in the measurement of the component of blood and urine and other substances.

2. Description of the Related Art

Known conventional devices used to assay of liquid sample are (1) assay devices for which filter paper is cut to a specified size, and is made to absorb the reagent that is to react with the sample, then the filter paper is attached to a support, and (2) assay devices for which gelatin containing the reagent is formed into a specified shape, then attached to a support. After preparing the assay device, the liquid samples are required to drop on the filter paper or the gelatin for assay.

The above-noted assay devices, however, require that the manufacturing process include the cutting and attaching of filter paper or gelatin. This does not allow refinement of the assay elements that hold the reagent, which, in turn, does not allow the miniaturization of the assay device as a whole, compared with its current form. Moreover, to enable the assay of a multiplicity of items using a single assay device, the above-noted conventional assay devices require the cutting and attaching of a multiplicity of filter paper or gelatins, thereby increasing the number of steps in the manufacturing process and increasing the manufacturing costs.

SUMMARY OF THE INVENTION

Therefore, the first object of this invention is to provide an assay device in which the assay elements that hold the sample have been refined. The second object of this invention is to provide an assay device manufactured with a multiplicity of assay elements, using few steps. The third object of this invention is to provide an assay device in which the detector and the part on which the sample is applied are separated from each other.

To achieve the objects described above, the liquid assay device of this invention comprises:

a support composed of an organic macromolecule, said support having a surface divided into two areas located adjacent to each other;

a divider in the surface, defining the border of both areas to separate a first area from a second area;

a detection layer affixed to the first area and containing a reagent; and a water-swelling layer affixed to the second area, said water-swelling layer expanding by absorbing water.

To assay liquid samples using this device, a drop of the liquid sample is applied to the water-swelling layer. When the drop is applied, the water-swelling layer expands, extending over the divider and coming into contact with the detection layer. The liquid sample then moves by capillarity from the water-swelling layer to the detection layer, where it reacts with the reagent. If the reagent is such that it produces color or emits light when reacting to specific components, the components contained within the sample can be identified using optical methods. Depending on the properties of the reagent, other methods may also be used to identify components in the sample.

The detection layer of the device of this invention is separated from the location (the water-swelling layer) where the sample is dropped to, so when the sample is flowing from the water-swelling layer to the detection layer, a specific component within the sample can be removed from the sample. An example would be separating out the corpuscles when blood is being assayed. Moreover, a second reagent, that differs from the reagent contained in the detection layer, can be put in the water-swelling layer.

When the divider is composed of a water-repellent material, the reagent contained in the detection layer will not flow over onto the water-swelling layer until the reagent reacts with the sample, even if said reagent is a liquid.

A suitable method for manufacturing the device of this invention comprises the following steps:

(a) reforming the perimeter of a specific area on a surface of a support composed of an organic macromolecule so as to render it hydrophilic;

(b) forming a divider composed of a water-repellent material on the reformed perimeter;

(c) reforming the specific area and other area adjacent to the divider so as to render them hydrophilic;

(d) affixing a detection layer and a water-swelling layer to the reformed specific area and another reformed area respectively, said detection layer containing reagent, said water-swelling layer expanding by absorbing water.

This invention enables the refinement of the detection layer, by using the hydrophilic properties of the support to make a detection layer, a divider, and a water-swelling layer. Moreover, manufacturing costs are low, because there is no cutting and attaching work in the manufacturing process and a multiplicity of detection layers can be affixed simultaneously.

DESCRIPTION OF THE PREFERRED EMBODIMENTS

An actual embodiment of this invention will be explained along with drawings. FIG. 1 shows the processing order used to manufacture the device of this invention.

First, the organic macromolecule materials that are to comprise the support and the shape of the support are chosen. One or more of the following substances can be used as the organic macromolecule molecule: polyethylene, polypropylene, polystyrene, ABS, poly(vinyl chloride), poly (vinylidene chloride), thermoplastic polyurethane, poly (methyl methacrylate), polyoxyethylene, polycarbonate, polyamide, acetal resin, poly(phenyleneoxide), poly (butyleneterephthalate), poly(ethylene terephthalate), poly (phenylene sulfide), or other thermoplastic resins; unsaturated polyester resin, epoxy resin, phenol resin, urea resin, melamine resin, diallyl phthalate resin, or other thermosetting resins; styrene-butadiene rubber, polyisoprene rubber, natural rubber, or other rubbers. The shape of the support can be of sheet form, column form, cylinder form, membrane form, or any form that provides the areas on which to affix the detection layer and water-swelling layer.

Figure 1A:
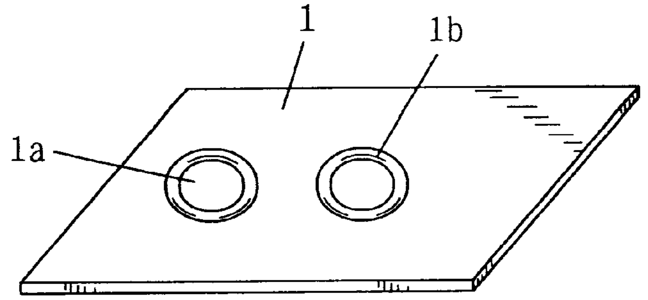
FIGS. 1A, 1B, 1C, 1D and 1E are perspective views that show the manufacturing process of an actual embodiment of the assay device.

As shown in drawing FIG. 1A, the first areas 1*a*, where the detection layer is to be affixed, and the second area (to be explained below), where the water-swelling layer is to be affixed, are specified on the surface of the support 1, which is composed of organic macromolecule. In this example, the first areas are round in shape and the second area is a rectangle surrounding the first areas. The perimeters 1*b* of the respective first areas 1*a* are reformed so as to render them hydrophilic. The following methods can be used to reform parts of the support so as to render them hydrophilic: chemical processing which masks the surface of hydrophobic organic macromolecule, then chemically introduces hydrophilic groups or graft branches into exposed areas (where the mask does not cover the organic macromolecule) to render only the exposed areas hydrophilic; or plasma processing; corona discharge processing; UV irradiation; or other processing. Of these methods, irradiation with UV rays works well, because it requires no special pre- or post-processing and the necessary equipment is simple. A low-pressure mercury lamp is an ideal optimal source for the UV rays, because it has a low tube-wall temperature of approximately 100° C. and radiates high-energy, short wavelength UV rays. Short wavelength UV rays of 185 nm are good, because they have high energy, with the next best wave length being 254 nm. Irradiation should normally take place for a time period of from 1 to 120 minutes, at an irradiation distance of between 0.5 and 8 cm, and an illumination intensity of from 1 to 20 $mW/cm^2$.

Figure 1B:
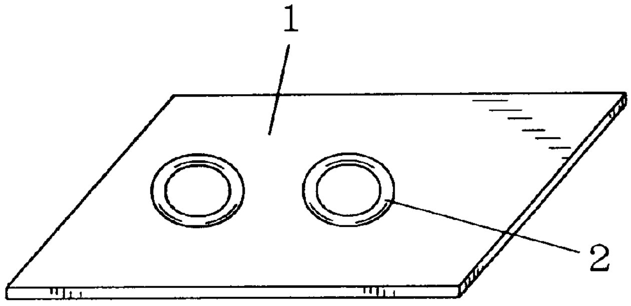

Next, as shown in drawing FIG. 1B, dividers 2 composed of water-repellent material are formed on the reformed perimeters 1*b*. Good substance to use as the water-repellent material is a resin containing a function group that is bondable with carboxyl group or hydroxyl group, or a surface active agent. This is because molecules existing on the surface of the organic macromolecule prior to reforming, even carbon or hydrogen, are often substituted by the reforming into carboxyl or hydroxyl group. So, if the water-repellent material is a resin containing a function group that bonds chemically or physically with these molecules or if it is a surface active agent, it bonds with the reformed perimeter areas 1*b* and easily forms the dividers 2. Many kinds of this type of water-repellent material are known, such as silane coupling agent, fluorine compounded acrylic copolymer emulsion, amino-group denatured silicon oil, silane coupling agent—fluoroalkyl silicon chloride mixture, polyoxyalkylene denatured silicon oil, fluorine-based surface active agent, or fluorine silicon surface active agent.

Figure 1C:
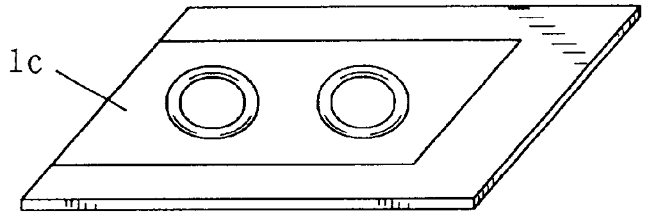
Figure 1D:
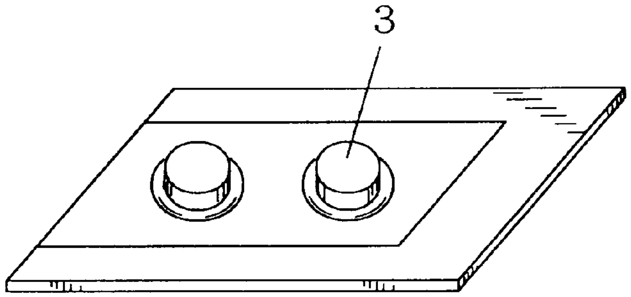

Following the formation of dividers 2, as shown in drawing FIG. 1C, the first areas 1*a*, which are surrounded by the dividers 2, and the rectangular second area 1*c*, which encloses the dividers 2, are reformed so as to render them hydrophilic. If UV irradiation is used to conduct the reforming, as noted above, a fluorine based or silicon based substance is good as the water-repellent material that composes the divider 2. This is because fluorine-based and silicon-based substances are inactive when exposed to UV light, so the function of the dividers 2 is not diminished by UV rays. The areas 1*a* and 1*c* may be reformed simultaneously, or separately with using a mask to block the UV rays. Even when the reforming is carried out separately for each area, if a fluorine or silicon based substance is used as the water-repellent material, the precision of the mask pattern is not required so strictly.

Figure 1E:
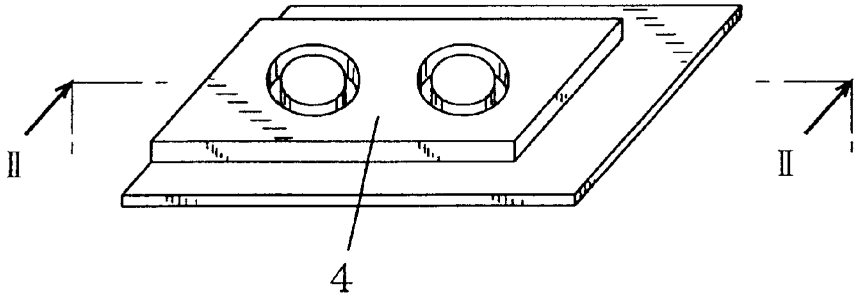

Finally, a liquid made by solving the reagent is applied to the first areas 1*a* (drawing FIG. 1D) and gel composed of water-swelling material is applied to the second area 1*c* (drawing FIG. 1E). The water-swelling material can be, for example, water-absorptive resin, clay, or other inorganic compound in layer form. The liquid applied to the first areas 1*a* dries to become the detection layer 3. The gel applied to the second area 1*c* dries to become the water-swelling layer 4. The areas 1*a* and 1*c* can have their respective liquids applied simultaneously or one at a time.

Figure 2:
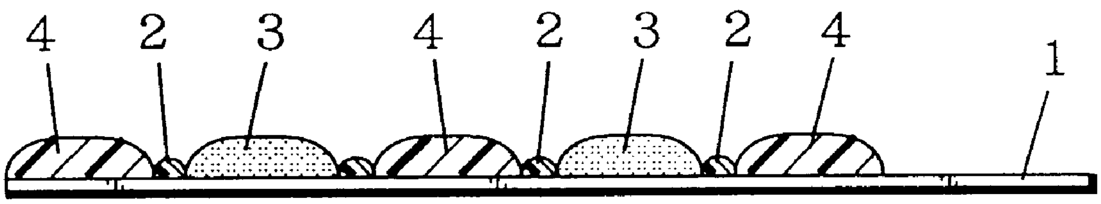
FIG. 2 is a sectional view of the assay device, taken along line II—II of FIG. 1E.
Figure 3:
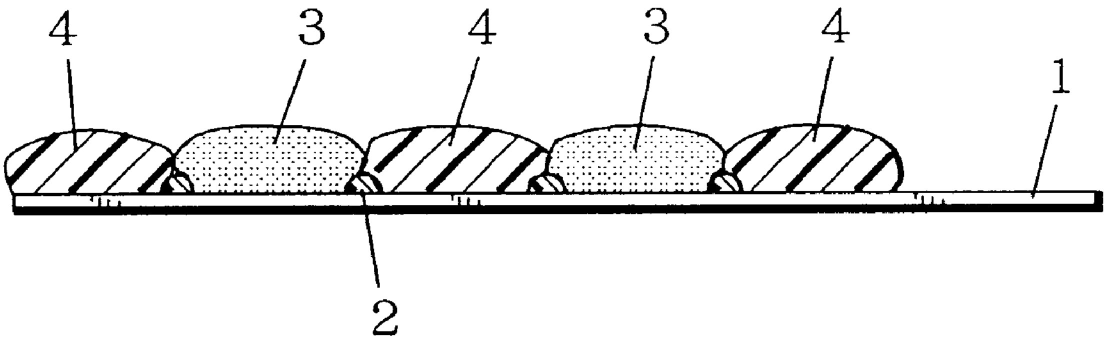
FIG. 3 is a sectional view of the assay device in a operating condition, taken along line II—II of FIG. 1E.

A perspective view diagram of the assay device obtained via the above-noted processes is shown in FIG. 1E. FIG. 2 is a sectional view taken on the line II—II of FIG. 1E. When this device is used to conduct an assay, drops of the liquid sample are applied onto the water-swelling layer 4. When the drops are applied, the water-swelling layer expands, extending over the dividers 2 and coming into contact with the detection layers 3. The liquid sample then moves by capillarity from the water-swelling layer 4 to the detection layer 3, where it reacts with the reagent. FIG. 3 shows the water-swelling layer 4 swelling and the detection layer 3 reacting with the liquid sample. To enable the assay of a multiplicity of items using a single assay device, a multiplicity of detection layers 3 may be made on a single support 1, each surrounded individually within a multiplicity of closed dividers 2 on the support 1. The drawings show a device made with the objective of simultaneously assaying two items. This enables the liquid sample to simultaneously flow from the water-swelling layer 4 into a multiplicity of detection layers 3, where it reacts separately with each of the reagent.

What is claimed is:

1. A device for assay of a liquid sample, said device comprising:

a support composed of an organic macromolecule, said support having a surface divided into at least two areas located adjacent to each other;

a divider on the surface defining a border between said two areas to separate the first area from the second area;

a detection layer affixed to the first area and containing a reagent; and a water-swelling layer affixed to the second area, said water-swelling layer being capable of expanding by absorbing water when a water-containing liquid sample is applied to the water-swelling layer to extend a part of the water-swelling layer over the divider and into contact with the detection layer, said divider preventing the water-swelling layer from completely covering the detection layer so that a portion of the detection layer remains exposed, the liquid sample moving by capillarity from the water-swelling layer to the detection layer where it reacts with the reagent, thereby permitting the reaction in the detection layer to be identified optically.

2. The device of claim 1, wherein the divider is composed of a water-repellent material.

3. The device of claim 1, wherein the water-swelling layer comprises principally a water-swelling, water-absorptive resin.

4. The device of claim 1, wherein the second area surrounds the first area.

5. The device of claim 1, wherein the water-swelling layer contains a second reagent that is different from said reagent contained in the detection layer.

6. The device of claim 1, wherein the organic macromolecule is a thermoplastic resin, a thermosetting resin, or a rubber, or a combination thereof.

7. The device of claim 1, comprising a multiplicity of first areas each containing a detection layer and the water-swelling layer of the second surrounds the multiplicity of detection layers of the first areas.

8. The device of claim 2, wherein the divider extends upwardly from said support to a point above the surface thereof and between said two areas.

* * * * *